United States Patent [19]

Etkin

[11] Patent Number: 4,657,667
[45] Date of Patent: Apr. 14, 1987

[54] PARTICLE CLASSIFIER

[75] Inventor: Bernard Etkin, Willowdale, Canada

[73] Assignee: The University of Toronto Innovations Foundation, Toronto, Canada

[21] Appl. No.: 596,952

[22] Filed: Apr. 5, 1984

[51] Int. Cl.[4] .................. B07B 7/086; B07B 11/04; B07B 11/06

[52] U.S. Cl. .................. 209/135; 209/143; 209/154

[58] Field of Search .............. 209/136, 134, 135, 137, 209/154, 143

[56] References Cited

U.S. PATENT DOCUMENTS

| | | | |
|---|---|---|---|
| 2,694,492 | 11/1954 | Rumpf et al. | 209/144 |
| 2,828,011 | 3/1958 | Whitby | 209/135 |
| 2,846,151 | 8/1958 | Wehn et al. | 241/14 |
| 2,999,563 | 9/1961 | Wehn et al. | 183/83 |
| 3,506,119 | 4/1970 | Rumpf et al. | 209/139 |
| 3,952,207 | 4/1976 | Leschonski et al. | 250/573 |
| 4,132,634 | 1/1979 | Rumpf et al. | 209/136 |
| 4,153,541 | 5/1979 | Rumpf et al. | 209/143 |
| 4,213,852 | 7/1980 | Etkin | 209/136 |
| 4,321,134 | 3/1982 | Leschonski et al. | 209/30 |

FOREIGN PATENT DOCUMENTS

| | | | |
|---|---|---|---|
| 522988 | 3/1956 | Canada . | |
| 611838 | 1/1961 | Canada . | |
| 828125 | 2/1938 | France | 209/137 |

Primary Examiner—Frank W. Lutter
Assistant Examiner—Thomas M. Lithgow
Attorney, Agent, or Firm—Hirons, Rogers & Scott

[57] ABSTRACT

A particle classifier has a uniform, laminar, classifying air stream and a duct to introduce particulate material generally perpendicular to the air stream. The particulate material is entrained in a secondary air stream that is diverted as it enters the classifying air stream by a curved surface. The curved surface produces and diverts the air stream by the Coanda effect to minimize disturbance to the classifying air and segregate the particles from the secondary air.

12 Claims, 4 Drawing Figures

PARTICLE CLASSIFIER

The present invention relates to devices for classifying particulate material according to the ratio of (drag) air resistance to mass (D/m). of the particle and in particular to such classifiers that utilise a flow of air to separate particles that differ from one another in size, density or shape, any of which leads to differences in D/m. In the processing of particulate materials it may be necessary to separate the material into different products according to size, density, or shape. This is known as classifying and enables dissimilar material to be separated such as iron ore from silicon, or a single material separated according to the nominal size or configuration, e.g. mica flakes from mica chunks.

Classifying may be accomplished in a number of ways but for fine particulate material it is common to rely on differences in aerodynamic drag to achieve the desired classification. In one form of classifier, the material is allowed to fall under the influence of gravity through a generally horizontal air flow, and differential displacements of the material in the direction of the air flow is the factor that separates particles having different ratios of drag to mass. Thus, by providing collection devices at different locations downstream of the point at which the material is introduced a classification of the material is achieved.

Such devices operate satisfactorily for face-flowing materials generally larger than about 500 microns, but for extremely small particles the throughput of the apparatus is limited owing to their low settling speed. It has been proposed to increase the throughput by entraining the material in a secondary airstream and introducing it into the classifier at high speed. However, the introduction of the secondary air flow tends to disturb the classifying airstream and is therefore detrimental to the performance of the classifier.

Attempts have been made to overcome this problem by creating low pressure zones adjacent to the inlet of the secondary airstream so that the secondary airstream is extracted after it has introduced the particulate material with the intent of minimising the disturbance. However this has not proven entirely satisfactory as inevitably there will be some disturbance to the airstream and the classifying stream is in any event disturbed by the introduction of the secondary air stream. Attempts have also been made to inject mechanically the particulate material but it is difficult to ensure uniform velocity at the point of introduction.

It is therefore an object of the present invention to provide a classifier in which the above disadvantages are obviated or mitigated.

According to the present invention there is provided a classifier for particulate material comprising a housing having an inlet to receive a classifying air flow, collection means downstream of said inlet to receive material classified by said air flow, and material introduction means intermediate said inlet and said collection means to introduce particles into said housing substantially perpendicular to said classifying air flow, said material introduction means including a material outlet aperture in a wall of said housing extending generally transversely of said air flow, conveying means to convey material entrained in a secondary air flow to said material outlet to introduce material into said housing and diverting means to divert said secondary air flow to a direction generally parallel to said classifying air flow, said diverting means including a surface extending downstream from said outlet and being dimensioned to divert said secondary airstream by a Coanda effect and thereby segregate said secondary airflow from said particles.

An embodiment of the present invention will now be described by way of example only with reference to the accompanying drawings in which FIG. 1 is a general perspective view of a particle classifier with portion sectioned for clarity.

Figure 1:
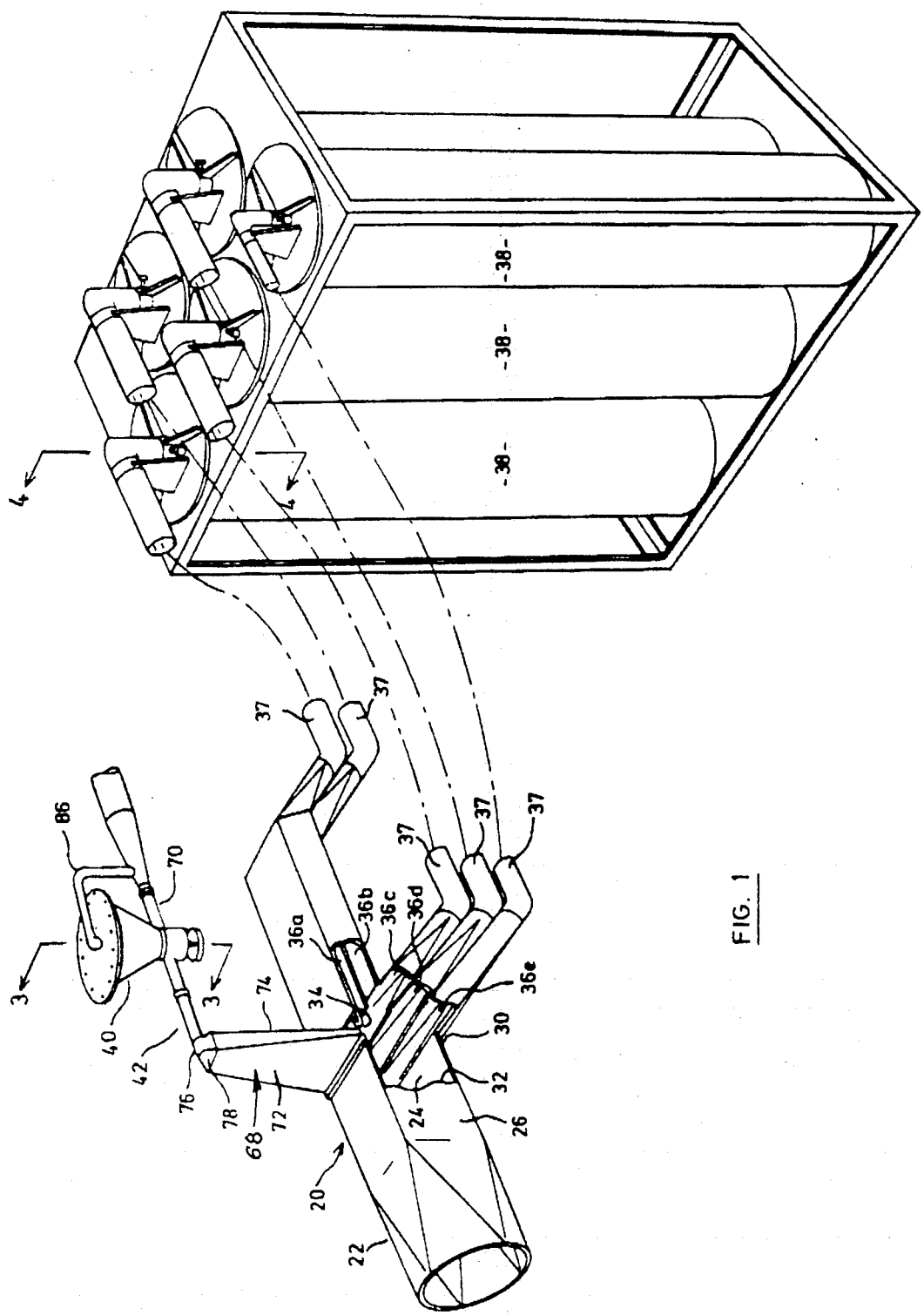

Referring now to FIG. 1, a classifier 20 includes an inlet duct 22 that delivers classifying air to the interior 24 of a housing 26. The inlet duct is shaped using state of art aerodynamics to provide a uniform and laminar flow pattern to the classifying air to prevent turbulence of the classifying air affecting the performance of the classifier. The housing 26 is formed from upper and lower walls 28, 30 respectively and side walls 32. The housing 26 has a generally rectangular cross-section and an elongated slit 34 is formed in the upper wall 28 and extends the full width thereof. The housing 26 splits into a plurality of discrete passages 36, in this case 5, designated by the suffixes a through e respectively, that provide collection means for the classified material. Each of the passages 36 is connected by a conduit 37 to a filter bag 38 of conventional construction so that particulate material entrained in the air entering the passage is retained within the filter bag 38 for subsequent removal.

The particulate material to be classified is contained within a hopper 40 and is introduced into the interior 24 of housing 2,6 by secondary air supplied through a supply conduit 42 that is connected to the slit 34. Thus material from the hopper is entrained within the secondary air and conveyed through the supply conduit 42 to the interior of the housing 26 where it is classified and enters one of the passages 36 for collection in the filter bag 38.

Figure 2:
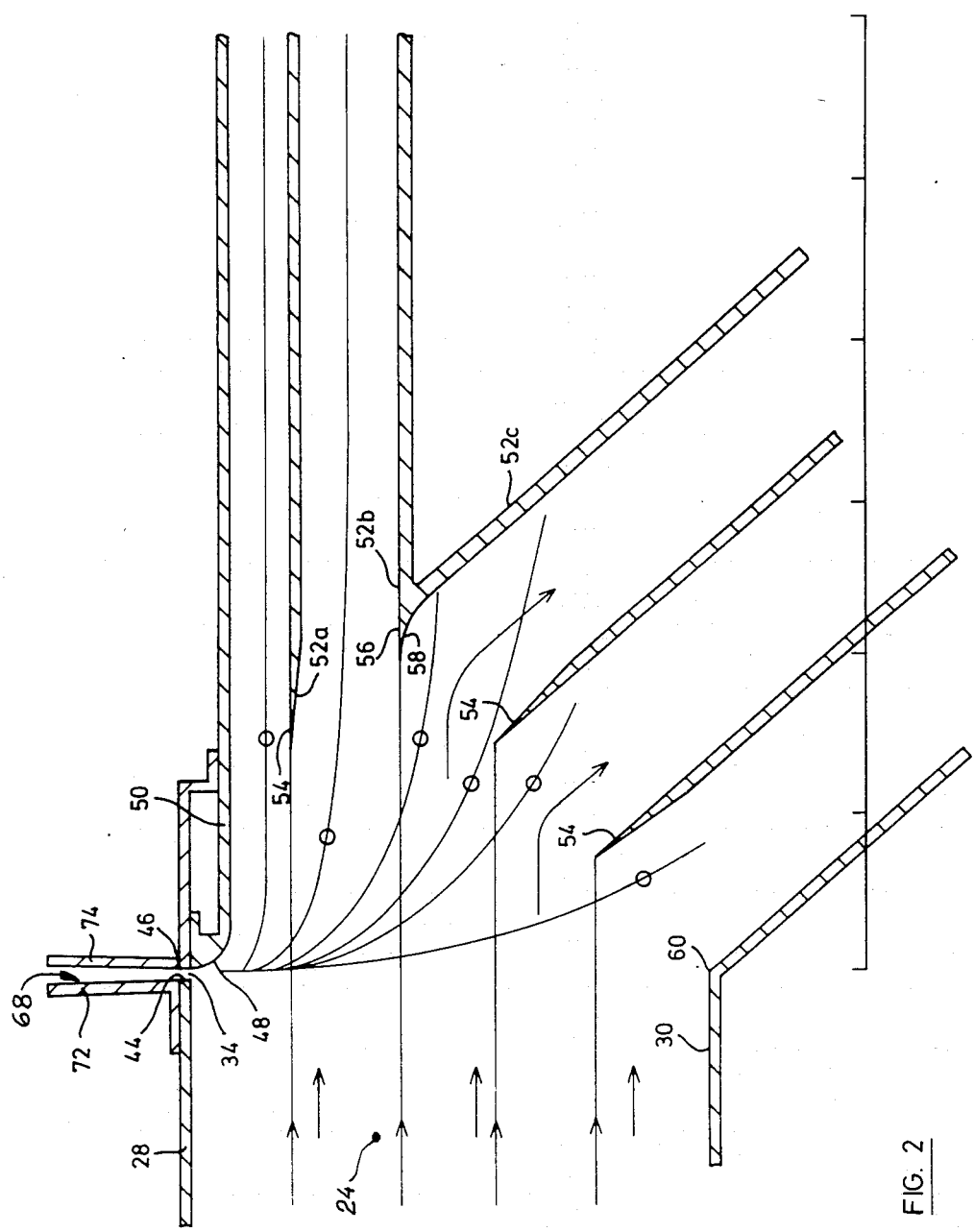
FIG. 2 is a section on the line 2.2, on an enlarged scale, of the classifier of FIG. 1.

The details of the introduction and classification of material can best be seen in FIG. 2. The slit 34 includes an upstream and downstream edge 44, 46 respectively. These edges extend across the full width of the upper wall 28 of the housing 26. A convexly curved surface 48 is positioned adjacent the downstream edge 46 and protrudes into the interior of the housing 26. The convex surface 48 extends through an angle of 90° and terminates in an upper partition 50 that serves as a continuation of the upper wall 28. The passages 36 are defined downstream of the convex surface 48 by partitions 52 that extend the full width of the housing 26. The leading edge 54 of each of the partitions 52 is tapered to provide a knife edge so that a minimum frontal area is presented to the particles that may impinge on it. The partitions 52a and 52b define the passages 36a and 36b respectively. These passages are generally aligned with the classifying airstream and therefore present a minimum disturbance to the flow of air through the passages.

The passages 36 c, d, and e are inclined at an angle to the direction of airflow. The partition 52c merges with the partition 52b to provide a nose 56 that has a downwardly curved upper surface 58. The partitions 52d and e are parallel to the partition 52c and the lower surface 30 is bent as indicated at 60 so that it extends parallel to the partition 52d. Thus the passages 36c, d and e are defined between parallel partitions and have a constant cross-sectional area.

Air flow through each of the passages 36 is controlled by a butterfly valve 62 located in the conduit 37. The valve 62 comprises a plate 64 that is connected to a spindle 66 for movement therewith. The mass flow in each passage is measured by a venturi 63 that has a pair of presure taps 65, 67. A transducer 61 provides a signal proportional to the differntial pressure at the two taps 65, 67 which forms input into a comparitor 69. The second input to the comparitor 69 is derived from a controller 71 and the error signal produced by the comparitor 69 is used to control a servomotor 73 connected to the spindle 66 and thus maintain the air flow at the rate determined by the controller 71. The butterfly valves 62 are used to control the mass flow in each of the passages and to provide a condition in which the mass flow through each passage is balanced in the same ratio as the area of the airstream intercepted by each passage. In this way the airstream intercepted by each passage is completely swallowed by that passage and a minimum of disturbance to the laminar air flow upstream of the slit is obtained.

Figure 3:
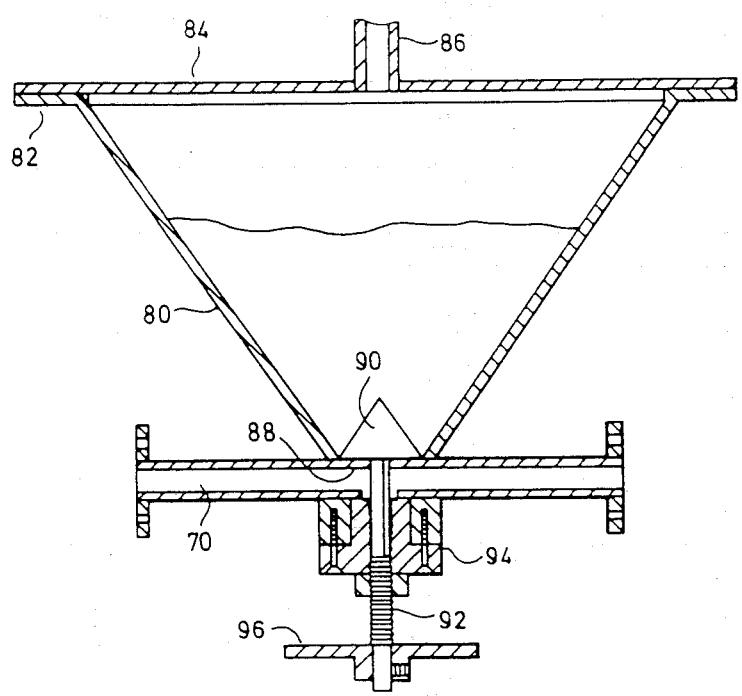
FIG. 3 is a sectional view on an enlarged scale on the line 3.3. of FIG. 1.
Figure 4:
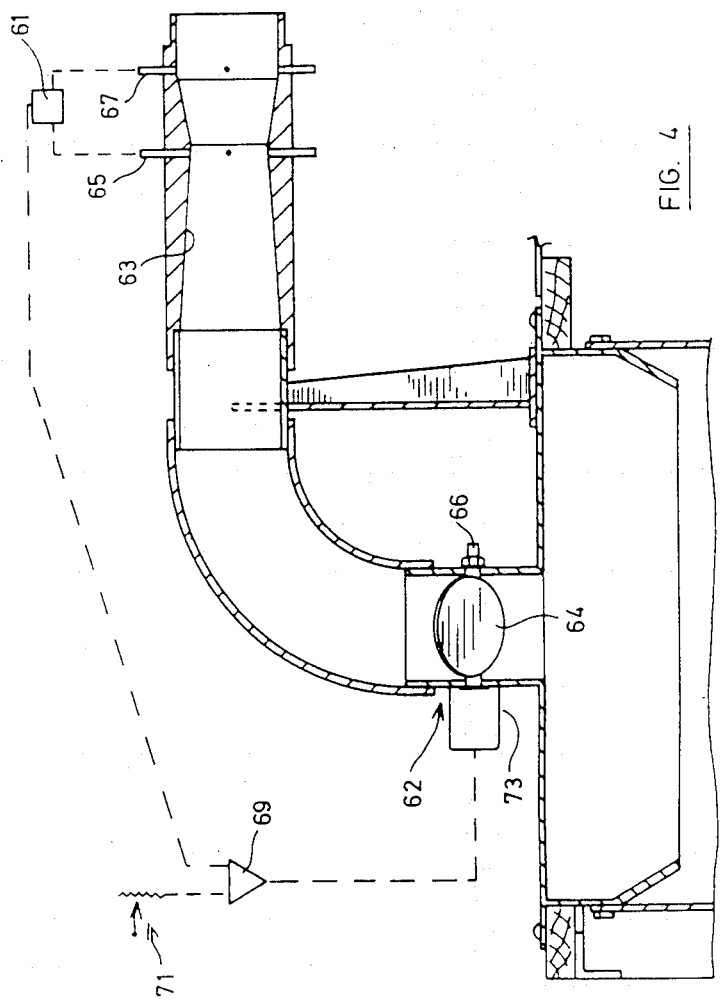
FIG. 4 is a sectional view on the line 4—4 of FIG. 1.

The particulate material is delivered to the slit 34 through the supply conduit 42 that includes a vertical duct 68 and a generally horizontal rectangular conduit 70. The duct 68 is defined between a pair of lateral walls 72, 74 that diverge away from the slit 34. The duct 68 is designed to provide a constant area cross-section and therefore as the walls diverge, the edges of the walls also converge toward one another. The ducts 68 and 70 are interconnected by an elbow 76 that includes an inclined surface 78 extending from the upstream lateral wall 72. Material is entrained in the secondary air supply provided to the supply conduit 32 by means of the hopper that is best seen in FIG. 3.

The hopper 40 includes a frusto conical body 80 having a horizontal flange 82 at its upper end. The flange 82 receives a cover plate 84 that is connected through a bleed pipe 86 to the secondary air supply. The lower end of the body 80 is centered over an aperture 88 in the rectangular duct 70 and flow from the hopper body 80 into the duct 70 is controlled by means of a valve member 90. The valve member 90 is mounted upon a threaded stem 92 that is rotatable within a boss 94. A handle 96 is provided to rotate the stem within the boss so that rotation of the stem moves the valve member 90 toward or away from the aperture to vary the spacing between the edge of the valve member 90 and the lower portion of the body 80. Air bled into the hopper through the bleed pipe 86 ensures an equalization of pressure across the material and so prevents the particulate material being dispersed within the hopper body 80.

In operation, the classifying air flow is fed to the interior of the housing 26 and the secondary air flow supplied to the supply conduit 42. The butterfly valves 62 are adjusted so that the mass flow in each of the passages 36 is in the correct ratio and so that the disturbance to the laminar air flow being presented to the interior of the housing is minimal.

The valve member 90 is then opened to allow particulate material to flow into the supply conduit 42 and be entrained in the secondary air supply. The entrained material impinges upon the inclined surface 78 in the elbow 76 and thereby undergoes an abrupt change of direction that will tend to break down any agglomerations that may occur in the material. The material is then fed in a uniform fashion through the vertical duct 68 to issue from the slit 34 at relatively high speed in a direction generally perpendicular to the direction of flow of the classifying air. The width of the slit and the curvature of the surface 48 are chosen such that the secondary airstream is subject to the Coanda effect which will divert the secondary airstream through 90° so that it flows parallel to the classifying air flow without interfering with it. The relatively high velocity of the secondary air stream imparts sufficient momentum to the particles that they segregate from the secondary air stream and are projected into the classifying airstream at a uniform velocity. The differences in D/m between the different size particles cause the particles to take different trajectories which will fall into one of the passages 36. From there the particles pass into the filters 38 where the particles are collected as the air is dispersed to the atmosphere.

By ensuring that the secondary airstream is diverted by the convex surface under the influence of the Coanda effect there is no separation of the secondary airstream from the adjacent wall 48 and the disturbance to the classifying airstream is also kept at a minimum.

The trajectory of the different size particles can be predicted and so it is possible to place the leading edge 54 of each of the partitions 52 at a point that will provide the desired cut size of the particles. The partitions 52 are orientated such that they are generally parallel to the trajectory of the particles that will fall within the passages and thus the tendency of the particles to bounce backward out of the passages is minimized.

It has been found that satisfactory results can be obtained with the classifying and secondary air flow of similar velocity, in some experimental tests in the order of ten meters per second. Flows in the range 5–30 M/S could be used and the ratio between the flow rates may vary from ½ to 2. The radius of the Coanda bend 48 must be chosen small enough to ensure that the particles to be separated cannot negotiate the turn, and therefore separate from the secondary air flow to enter into the classifying air. The relative dimensions between the width of the slit 34 and the radius of the surface 48 to produce the Coanda effect are well established and it has been found that a slit having a width of 1.5 mm will operate satisfactorily with a convex surface having a radius of 6 mm.

In the experimental apparatus that has been tested to date the leading edges of the partitions 52*c*, *d* and *e* have been disposed on a common line extending at an included angle of 41° from the lower surface 30. The position of the leading edges can be chosen to select the desired cut size or alternatively the mean velocity of either the secondary air or the classifying air may be changed to vary the cut size with fixed partitions.

The use of the butterfly valves in the ducts 38 ensures that minimum disturbance occurs to the laminar classifying flow whilst maintaining complete "swallowing" of the airstream.

With the apparatus described above, it has been found that particles of less than 200 micron nominal diameter can be classified with a high level of accuracy down to 10 microns or less. Further the throughputs obtained are similar to those obtained with machines intended to operate on larger particle sizes.

Whilst a curved surface 48 has been disclosed, it will be appreciated that other surface configurations may be used to produce the desired effect such as a series of planar faces approximating to a curve.

I claim:

1. A classifier for particulate material comprising a housing having an inlet to receive a classifying air flow flowing in a given direction, collection means downstream of said inlet to receive material classified by said air flow, and material introduction means intermediate said inlet and said collection means to introduce particles entrained in a secondary air stream into said housing in a direction other than said given direction, said material introduction means including a material outlet aperture in a wall of said housing extending generally perpendicular to said given direction, conveying means to convey material and said secondary air stream to said material outlet and diverting means to divert said secondary air stream to a direction generally parallel to said classifying air flow flowing in said given direction, said diverting means including a surface extending downstream from said outlet and adjacent thereto and being dimensioned to divert said secondary airstream by a Coanda effect generally parallel to said given direction and thereby segregate said secondary air/stream from said particles and permit continued movement of said particles along predictable trajectories.

2. A classifier according to claim 1 wherein said surface is curved.

3. A classifier according to claim 2 wherein said material outlet is an elongated slit and said curved surface extends from a downstream edge of said slit to merge smoothly with an adjacent wall of said housing.

4. A classifier according to claim 3 wherein said conveying means includes a duct having a pair of laterally extending walls coincident with the lateral edges of said slit.

5. A classifier according to claim 4 wherein said duct is of constant cross section and said walls diverge away from said slit.

6. A classifier according to claim 5 wherein said duct includes an abrupt change in direction to reduce agglomeration of said material.

7. A classifier according to claim 3 wherein said collection means includes a plurality of discrete passages each having an inlet defined by a pair of parallel partitions having their leading edges generally transverse to the direction of introduction of said material.

8. A classifier according to claim 7 wherein each of said passages includes flow control means to adjust the flow rate in each passage and maintain the ratio of the flow rates in said passages proportional to the ratio of the area of said classifying flow intercepted by said partitions of each passage.

9. A classifier according to claim 7 wherein each of said partitions has a tapered leading edge to present a knife edge to said classifying air flow.

10. A classifier according to claim 9 wherein at least some of said partitions are oriented so that the axis of the passage defined between such partitions is generally parallel to the trajectory of a particle of material entering said passage.

11. A classifier according to claim 2 wherein said curved surface is of constant radius and extends through 90°.

12. A classifier for particulate material comprising a generally horizontal housing having an inlet to receive a classifying air flow flowing in a given direction, a collection means downstream of said inlet to receive classified material, an elongate slit in an upper surface of said housing extending generally perpendicular to the direction of said classifying air flow, material introduction means intermediate said inlet and said collection means to introduce particles entrained in a secondary air stream into said housing, a flow diverting surface projecting into said housing from a downstream edge of said slit, said material introduction means arranged to deliver said material entrained in the secondary air stream to said slit in a generally vertical direction, said slit and said diverting surface being selected to divert said secondary air stream through substantially 90° to a direction parallel with said classifying air flow by virtue of the Coanda effect produced on said secondary air stream by said diverting surface.

* * * * *